(12) United States Patent
Ward et al.

(10) Patent No.: US 7,976,466 B2
(45) Date of Patent: Jul. 12, 2011

(54) USE OF MULTIPLE DATA POINTS AND FILTERING IN AN ANALYTE SENSOR

(75) Inventors: W. Kenneth Ward, Portland, OR (US); Peter G. Jacobs, Portland, OR (US)

(73) Assignee: Isense Corporation, Wilsonville, OR (US)

( * ) Notice: Subject to any disclaimer, the term of this patent is extended or adjusted under 35 U.S.C. 154(b) by 1441 days.

(21) Appl. No.: 11/421,564

(22) Filed: Jun. 1, 2006

(65) Prior Publication Data

US 2006/0281985 A1 Dec. 14, 2006

Related U.S. Application Data

(60) Provisional application No. 60/687,199, filed on Jun. 2, 2005.

(51) Int. Cl.
*A61B 5/00* (2006.01)
(52) U.S. Cl. .................................. 600/365; 600/309
(58) Field of Classification Search .................. 600/347, 600/365
See application file for complete search history.

(56) References Cited

U.S. PATENT DOCUMENTS

| | | | | |
|---|---|---|---|---|
| 5,448,992 A * | 9/1995 | Kupershmidt | ................ | 600/347 |
| 6,135,952 A * | 10/2000 | Coetzee | ........................ | 600/336 |
| 6,253,097 B1 * | 6/2001 | Aronow et al. | ................ | 600/310 |
| 6,565,509 B1 | 5/2003 | Say et al. | | |
| 6,714,803 B1 | 3/2004 | Mortz | | |
| 2004/0133086 A1 * | 7/2004 | Ciurczak et al. | ............. | 600/322 |
| 2005/0027463 A1 | 2/2005 | Goode, Jr. | | |
| 2006/0264719 A1 * | 11/2006 | Schurman et al. | ............ | 600/316 |

* cited by examiner

*Primary Examiner* — Patricia C Mallari
(74) *Attorney, Agent, or Firm* — Schwabe, Williamson & Wyatt, P.C.

(57) ABSTRACT

Embodiments of the present invention improve the accuracy of measurements and/or in vivo calibrations of a biosensor by (1) using more than one sensor signal value and/or more than one directly sampled and measured value, such as a capillary blood glucose value, and/or by (2) delaying the acquisition of a sensor output value that is compared with a directly sampled and measured value, such as a capillary blood glucose value, during a calibration. In an embodiment of the present invention, the median of a series of measured values, or a median or mean of the medians, may be utilized to provide more consistent and accurate measurement data and/or to compensate for error or artifact.

18 Claims, 4 Drawing Sheets

| Seconds | 0 | 10 | 20 | 30 | 40 | 50 | 60 | 70 | 80 | 90 | 100 | 110 | 120 |
|---|---|---|---|---|---|---|---|---|---|---|---|---|---|
| Raw Current, nA | | 40 | 42 | 44 | *90* | 46 | 44 | 41 | 44 | 44 | 45 | 47 | 50 |
| Minute | | | | 1.00 | | | | | | 2.00 | | | |
| Interval Median | | | | 44.00 | | | | | | 44.50 | | | |
| Interval Mean | | | | 51.00 | | | | | | 45.17 | | | |

| 130 | 140 | 150 | 160 | 170 | 180 | 190 | 200 | 210 | 220 | 230 | 240 |
|---|---|---|---|---|---|---|---|---|---|---|---|
| 42 | 43 | *10* | *15* | 40 | 42 | 41 | 40 | 46 | 43 | 42 | 39 |
| | | 3.00 | | | | | | 4.00 | | | |
| | | 41.00 | | | | | | 41.50 | | | |
| | | 32.00 | | | | | | 41.83 | | | |

| 250 | 260 | 270 | 280 | 290 | 300 | 310 | 320 | 330 | 340 | 350 | 360 |
|---|---|---|---|---|---|---|---|---|---|---|---|
| 40 | 42 | 40 | 40 | 41 | 44 | 43 | 40 | 41 | 40 | *80* | *90* |
| | | 5.00 | | | | | | 6.00 | | | |
| | | 40.50 | | | | | | 42.00 | | | |
| | | 41.17 | | | | | | 55.67 | | | |

*Apparent Sensitivity = (sensor output − background) / CBG = 1.49 nA/(mg/dl)*

*Calculated Glucose = (sensor output − background) / Sensitivity = 66 mg/dl*

FIG. 5

| Seconds | 0 | 10 | 20 | 30 | 40 | 50 | 60 | 70 | 80 | 90 | 100 | 110 | 120 |
|---|---|---|---|---|---|---|---|---|---|---|---|---|---|
| Raw Current, nA | | 40 | 42 | 44 | *90* | 46 | 44 | 41 | 44 | 44 | 45 | 47 | 50 |
| Minute | | 1.00 | | | | | | 2.00 | | | | | |
| Interval Median | | 44.00 | | | | | | 44.50 | | | | | |
| Interval Mean | | 51.00 | | | | | | 45.17 | | | | | |

| 130 | 140 | 150 | 160 | 170 | 180 | 190 | 200 | 210 | 220 | 230 | 240 |
|---|---|---|---|---|---|---|---|---|---|---|---|
| 42 | 43 | *10* | *15* | 40 | 42 | 41 | 40 | 46 | 43 | 42 | 39 |
| 3.00 | | | | | | 4.00 | | | | | |
| 41.00 | | | | | | 41.50 | | | | | |
| 32.00 | | | | | | 41.83 | | | | | |

| 250 | 260 | 270 | 280 | 290 | 300 | 310 | 320 | 330 | 340 | 350 | 360 |
|---|---|---|---|---|---|---|---|---|---|---|---|
| 40 | 42 | 40 | 40 | 41 | 44 | 43 | 40 | 41 | 40 | *80* | *90* |
| 5.00 | | | | | | 6.00 | | | | | |
| 40.50 | | | | | | 42.00 | | | | | |
| 41.17 | | | | | | 55.67 | | | | | |

USE OF MULTIPLE DATA POINTS AND FILTERING IN AN ANALYTE SENSOR

CROSS REFERENCE TO RELATED APPLICATIONS

The present application claims priority to U.S. Provisional Patent Application No. 60/687,199, filed Jun. 2, 2005, entitled "Use of Multiple Data Points to Perform a First Calibration and Subsequent Calibrations of an Analyte Sensor," the entire disclosure of which is hereby incorporated by reference in its entirety.

TECHNICAL FIELD

Embodiments of the present invention relate to the field of medical devices, more specifically, to data acquisition, analyte sensing, and related measurement and calibration methods.

BACKGROUND

Among the other unpleasant aspects of having the disorder diabetes mellitus is the need to frequently test one's blood glucose concentration. With current technology a diabetic patient must prick his own fingertip or other body part to withdraw blood.

A number of solutions have been directed at easing this discomfort and increasing monitoring and control by using an implantable or insertable sensor, for continuous glucose monitoring. Ease of use is not only an important consideration from the perspective of patient comfort, but also from the perspective of patient health. The easier it is for a patient to take his blood glucose level reading, the more frequently he is likely to do so. In turn, with more frequent measurements, the patient is likely to do a better job at regulating his glucose level and thereby avoiding chronic complications in which body tissue is damaged by toxic glucose levels or acute complications in which the patient is in danger of entering a state of hypoglycemic shock. Moreover, by more frequently measuring his or her glucose levels, the patient will likely form a better understanding of his body's response to the consumption of varying types of food and of varying degrees of physical exertion. The better the patient understands his body's response characteristics the better he will be able to tailor his eating, exercise and insulin injection or ingestion regime. In addition to the frequency of measurement, the accuracy of the measurements that are taken is also of great importance.

BRIEF DESCRIPTION OF THE DRAWINGS

Embodiments of the present invention will be readily understood by the following detailed description in conjunction with the accompanying drawings. To facilitate this description, like reference numerals designate like structural elements. Embodiments of the invention are illustrated by way of example and not by way of limitation in the figures of the accompanying drawings.

FIG. 5 illustrates table of data showing the interval medians and interval means for a series of raw current values in accordance with an embodiment of the present invention;

DETAILED DESCRIPTION OF EMBODIMENTS OF THE INVENTION

Figure 1:
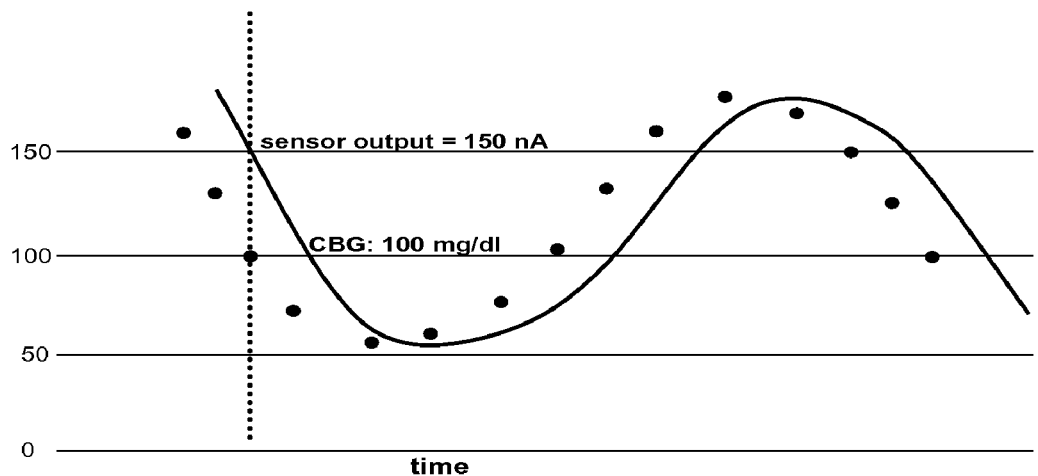
FIG. 1 illustrates a graph of capillary blood glucose (CBG) values and sensor output values with a calibration point occurring at a time when glucose is declining rapidly.

In the following detailed description, reference is made to the accompanying drawings which form a part hereof wherein like numerals designate like parts throughout, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

For the purposes of the present invention, the phrase "A/B" means A or B. For the purposes of the present invention, the phrase "A and/or B" means "(A), (B), or (A and B)". For the purposes of the present invention, the phrase "at least one of A, B, and C" means "(A), (B), (C), (A and B), (A and C), (B and C), or (A, B and C)". For the purposes of the present invention, the phrase "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

Embodiments of the present invention improve the accuracy of in vivo calibrations of a biosensor by (1) using more than one sensor signal value and/or more than one capillary blood glucose value, and/or by (2) delaying the acquisition of a sensor output value that is compared with a capillary blood glucose value during a calibration. In an embodiment of the present invention, the median of a series of measured values, or a median of the medians or of the means, may be utilized to provide more consistent and accurate measurement data and/or or to compensate for error or artifact. A filter may be used in a calibration method, and/or may be used to compensate for error during analyte sensing after calibration.

While the analyte of interest mentioned above and used herein throughout as an exemplary analyte is glucose, embodiments of the present invention may be utilized in conjunction with the measurement of other analytes, for example lactate. Furthermore, by utilizing more than one enzyme in a biosensor, more than one analyte may be measured using the same device, and/or may be calibrated in accordance with embodiments of the present invention.

In an embodiment of the present invention, in order to create a calibration, delay of the sensor output may be taken into consideration. In a further embodiment, a calibration method may use a single point or multi-point method, separate from, or in conjunction, with accounting for sensor output delay. In an embodiment, using a timeshift method of calibration for high rate of change glucose values to account for delay in sensor output may improve the accuracy of sensor estimation of glucose compared to calibration without timeshifting.

The use of a multi-point calibration system as opposed to a single point calibration system in accordance with embodiments of the present invention provides some benefits to a user. As more and more data are collected during the period of time that a biosensor is present in a mammal, the abundance of data may provide valuable information that may assist proper calibration of the device.

As an example, assume that a subject obtains capillary fingerstick blood samples twice per day and wears an indwelling glucose sensor for 5 days. After the morning calibration at the beginning of the third day, the subject has had a total of 5 calibration values. Often, these calibration values may be obtained at greatly different glucose concentrations, providing valuable information.

In an embodiment of the present invention, rather than use just one of these blood glucose values (accompanied by a sensor signal obtained a few minutes afterward), one can perform a multi-point calibration, in which all of, or at least a plurality of, the blood glucose and sensor signal pairings may be used. According to an embodiment, a regression line may be calculated that relates all of these data, with sensor signals being plotted on the Y-axis and the capillary blood glucose values being plotted on the X-axis. In an embodiment, a regression line may then be drawn and the slope of that line becomes the sensitivity value used in the calibration. In an embodiment, the sensor signal value at zero glucose may be used as the Y-intercept for the equation of the line (standard linear regression formula: $S=mG+b$, with S being calculated sensor signal, m being the slope or sensitivity, G being the glucose value and b being the y-intercept (also called the offset or background current)). In an embodiment, values of the sensor signal obtained in vitro prior to implant at zero glucose may be used to provide additional values to estimate the value for b properly.

In an embodiment of the present invention, one may weight more recent calibration values more heavily than earlier values (temporal weighting). Use of the many points in this regard may be valuable, especially because a single point (either from the sensor signal or from the blood analyte measurement) may be fraught with inaccuracy, for example from a glucose meter used or from the sensor itself, or from some other error or artifact. In an embodiment, weighting may be accomplished by obtaining sensitivity values for a plurality of calibrations and then weighting the sensitivities, for example temporally.

The geometry of a biosensor may give rise to a time delay in analyte level measurement as compared to a directly measured sample. Biosensors that are placed in the subcutaneous space measure analytes (such as glucose) in the interstitial fluid (ISF). ISF is a liquid, similar to plasma in composition that bathes cells such as fat cells or adipocytes. An exemplary biosensor may have several membranes or layers applied over an electrode, such as a noble metal electrode. In an embodiment, the outermost membrane may be a permselective membrane whose purpose is to limit the rate of mass transfer of analyte, such as glucose, into the enzyme (sensing) layer, which may lie beneath the permselective membrane, that is, closer to the electrode. In an embodiment, underneath the enzyme layer may be a specificity membrane, whose purpose is to exclude interfering compounds from permeating through to the electrode, while at the same time, allowing hydrogen peroxide to permeate through, and to be oxidized by, the electrode.

Typically, a subcutaneous biosensor must be calibrated in vivo in order to provide for the user an accurate measurement of an analyte, such as glucose. Since ISF is not easily accessible, blood measurements of analyte are typically used for such calibration.

However, for example, there may be a delay between a change in the blood concentration of glucose and the time at which the biosensor registers that change. This delay consists of several factors. First, there may be a delay in the transfer of glucose from the blood capillary into the ISF. This transfer has been estimated to be from less than one minute to over 5 minutes, and these disparities in results are probably due to differences in methods. Second, there may be a delay in the permeation of glucose through the outer membranes that limit mass transport of glucose and allow permeation of oxygen. Third, after the glucose has reached the sensing (enzyme) layer containing glucose oxidase, there may be a short delay during which the glucose and oxygen are converted into gluconic acid and hydrogen peroxide. Fourth, there may be a delay during which hydrogen peroxide permeates through a specificity membrane located between the sensing (enzyme-containing) layer and the indicating electrode. Fifth, there may be a mathematical delay that results from the use of software or firmware filters.

In an embodiment, it may be beneficial to apply a median or mean filter to a series of values obtained over, for example, 4-8 minutes. In an embodiment, such a filter may successfully filter out sharp artifact such as that caused by rapid motion of the patient in whom the sensor is implanted. In an embodiment, the delay that such a filter may introduce, in minutes, is equal to $(n-1)/2$, in which n is the filter length in minutes. Such a filter may be applied during ongoing analyte sensing and/or during calibration.

In an embodiment of the present invention, the measurement time delay may be managed to enhance calibration accuracy. In an embodiment, during the process of calibration, the capillary blood glucose (CBG) value may be compared to a sensor output value in order to arrive at a sensitivity, which may then be used to interpret sensor output values in the future. This process of interpretation yields values derived from sensor readings that estimate glucose concentration.

In an embodiment, calibration accuracy may be improved if the delay, various sources of which are detailed above, is accounted for. One way of performing a calibration is to compare a CBG value with a sensor output value obtained at the same time. This method is flawed, however, because it does not account for the measurement delay. This problem may be especially problematic if the glucose values are changing rapidly.

FIG. 1 shows a plot of capillary blood glucose values (CBG) in solid circles and sensor output values in the solid curve. FIG. 1 shows a calibration point (dotted line) that occurs at a time that glucose is declining rapidly. In this case, one should assume a background current of 1 nA. A delay has been introduced; one can see that the sensor curve is delayed behind the CBG values.

Figure 2:
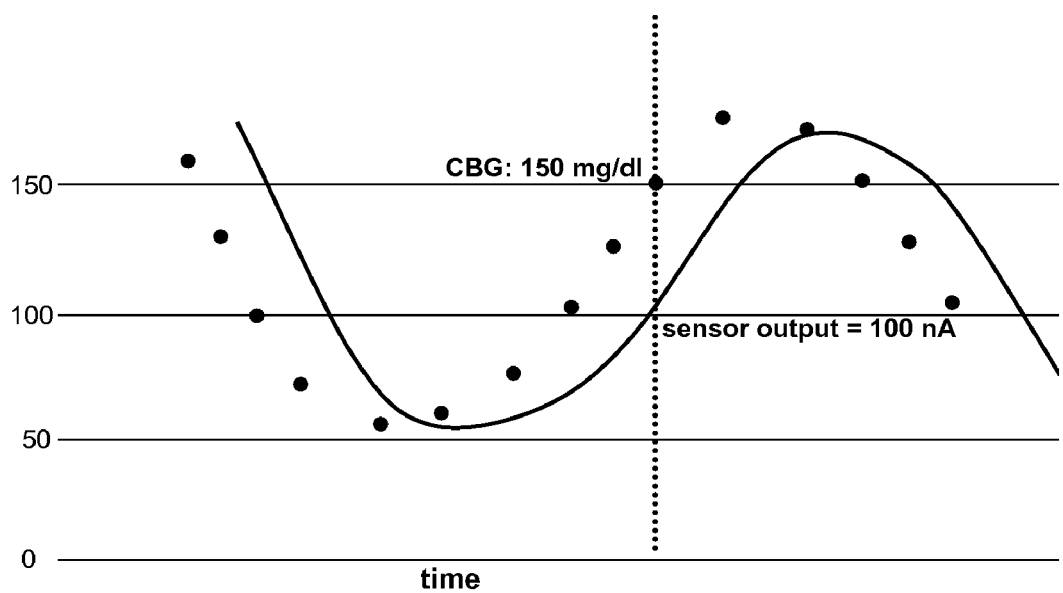
FIG. 2 illustrates a graph of capillary blood glucose (CBG) values and sensor output values with a calibration point occurring at a time when glucose is rising rapidly.

FIG. 2 shows how this apparent sensitivity (which now contains error due to delay) can give false information during a subsequent calculation of glucose at a time that glucose is rapidly rising.

Note that in FIG. 2, the actual CBG is 150 mg/dl, but the sensor calculates an errant value of 66 mg/dl. In fact, calculations of many scenarios will reveal that when one does not take into account sensor delay, then if one calibrates during falling glucose, one will systematically underestimate glucose level. The only time that there will be no error will be if the rate of change of glucose is exactly the same as the rate of change that occurred during the calibration.

Conversely, if one calibrates during rapidly rising glucose, one will systematically overestimate glucose level. Again, the only time that there will be no error will be when the rate of change is the same as the rate during calibration. A better method according to an embodiment of the present invention is to compare the current CBG value with a sensor output value obtained several minutes in the future, that duration being the same as the delay.

In an embodiment, one method that may be used to account for such a delay would be as follows: Assume that a CBG value is obtained at 6 PM. The sensor's Electronic Monitoring Unit (EMU) is given the CBG value either by the patient entering the CBG value that appeared on the glucose meter or by the glucose meter automatically entering the value into the EMU. At this point, the EMU does not perform a calibration, and instead simply waits for a period of time equal to the duration of the delay, say 5 minutes. Then, at 6:05, the EMU takes the signal (or a filtered reading acquired from a series of signals) from the biosensor and compares the delayed signal(s) with the CBG level obtained earlier. In an embodiment, this comparison may use a simple linear regression equation (using an appropriate background current value at zero glucose) or may use curve fitting equations that typify non-linear relationships between CBG and sensor output.

Accounting for this delay is especially important when the glucose signals are changing rapidly. This concept has been tested in a sample of data obtained from 13 patients with Type 1 diabetes. These sensors were then placed subcutaneously for 5 days. Each sensor acquired a reading of the electrical current output once per minute (1440 times per day) and sent this output value to an electronic monitoring unit. In addition, subjects measured their capillary blood glucose (CBG) at a fingertip 17-22 times per day using a hand held glucose meter (ROCHE ACCUCHEK). The capillary blood was also measured using a highly accurate benchtop machine, the SUPER GL glucose analyzer.

Figure 3:
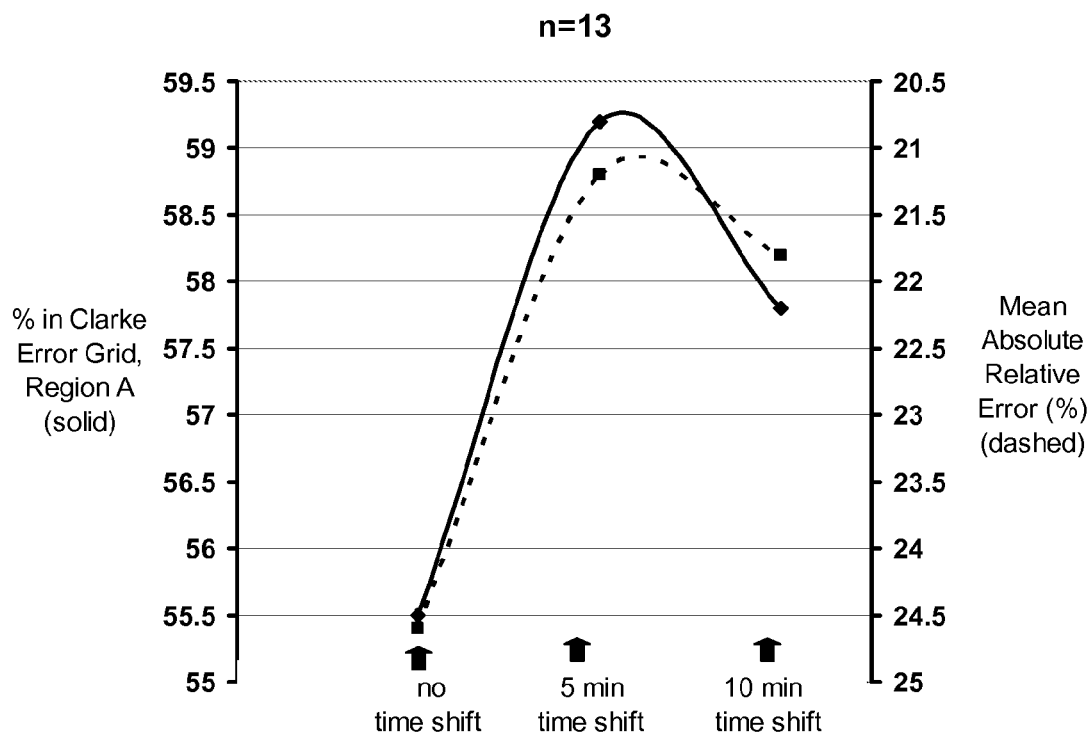
FIG. 3 illustrates a graph showing the effects of calibrating during rapidly changing glucose levels with data corrected and uncorrected for delay in accordance with various embodiments of the present invention.

Because there were a large number of CBG values obtained each day, the effect of calibrating during rapidly changing glucose levels could be tested easily. For this particular scenario, the data was examined retrospectively and calibration points were created twice per day, only when glucose level was falling at a very high rate (averaging 2.4 mg/dl per minute). FIG. 3 shows the results using such a calibration method, with data corrected and uncorrected for a delay. FIG. 3 demonstrates that when the sensor output was delayed by 5 minutes, the accuracy was greater than when no delay was used and when a delay of 10 minutes was used. In an embodiment, a delay of 4-10 minutes may be used. Accuracy was measured both as the percentage of data pairs that fell into the Clarke Error Grid Region A and as the Mean Absolute Relative Error (MARE). Absolute Relative Error for each pair is calculated as the absolute value of the difference between CBG and sensor glucose estimate, expressed as a percentage of the CBG. For these calculations, serial one-point calibrations were used twice per day.

In an embodiment, calibration may also be carried out by the use of many data pairs other than the most recent. In such a method, the prior history of data may be used in addition to using the present data.

The following table represents an example of a situation in which a multi-point calibration may lead to better accuracy than a single point calibration.

TABLE 1

| Calibration Number | Sensor Output Nanoamps (nA) | Measured CBG | Actual CBG |
| --- | --- | --- | --- |
| 1 | 10.5 | 100 | 100 |
| 2 | 19.5 | 200 | 200 |
| 3 | 23 | 250 | 250 |
| 4 | 30 | 305 | 305 |
| 5 | 40 | 411 | 411 |
| 6 | 20 | 220 | 220 |
| 7 | 21 | 260 | 200 |

Table 1 represents data from 7 successive calibrations. In all cases except the final calibration, the measured CBG is assumed to be accurate. On the final calibration (#7), there is a 30% error on the measurement of CBG.

In an embodiment, for each successive all point calibration, all of the points may be used to calculate a regression line. Specifically, in an embodiment, the most recent data pair (sensor output and CBG) may be double-weighted, the background current (not shown here) may be double-weighted, and all other data pairs may be single-weighted.

The sensitivities calculated for the first 6 calibrations are very similar regardless of whether one uses the multi-point method or a single-point method (in which only the current data pair is used to make the calibration). Sensitivity values using either method for calibrations 1-6 are very close to 0.09 nA/(mg/dl). However, when there is an errant CBG value (for example, due to improper use of a glucose meter or error of the glucose meter), as in calibration 7, a substantial error may result.

In an embodiment, using a multi-point calibration with the above-mentioned weighting, the sensitivity is calculated as 0.092 nA/(mg/dl). In contrast, using a single-point method with a background current assumed to be 1 nA, the sensitivity at calibration 7 is calculated as 0.077 nA/(mg/dl). In an embodiment, if one applies this errant sensitivity to an unknown, assuming no sensor error, the error would lead to a 15% absolute relative error.

Figure 4:
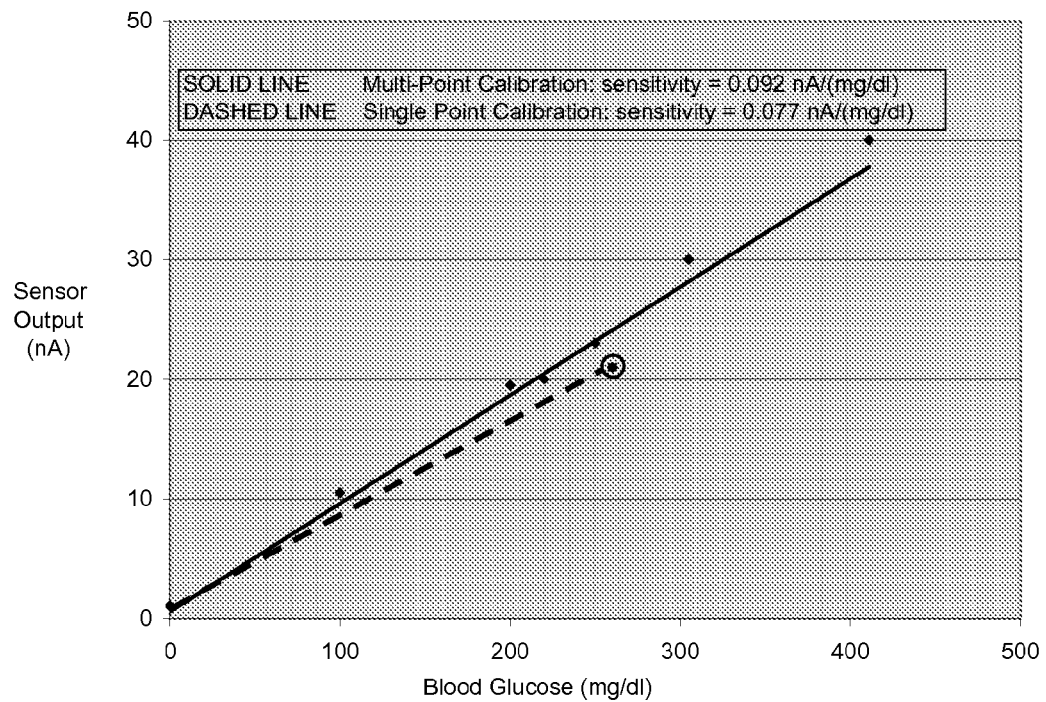
FIG. 4 illustrates a graph of sensor output and capillary blood glucose values indicating relative sensitivity of multipoint and single point calibration methods in accordance with an embodiment of the present invention.

A comparison of the sensitivity values calculated using the above-mentioned data is shown in FIG. 4. In FIG. 4, the data pair for the seventh data pair is shown as the circled point. The multi-point sensitivity (slope) is shown as the solid line and the single point sensitivity is shown as the dashed line.

In an embodiment of the present invention, another mechanism of using multiple points to arrive at a displayed data point during monitoring/sensing and/or calibration may be to obtain multiple data measurements and then to apply a mean or median filter to those data.

In an embodiment, there be a benefit to using median-based statistics as compared to mean-based statistics in a biosensor characterized by occasional error (artifact).

FIG. 5 is a table showing exemplary sensor measurements every ten seconds for a period of 360 seconds. Row 1 displays seconds of elapsed time. Row 2 displays the raw electrical current output of a biosensor (e.g. the output of an amperometric glucose sensor). Note the presence of erroneous values that are bolded and italicized.

Row 4 displays the median of 6 raw values obtained each minute, and Row 5 displays the mean value of the 6 raw values obtained each minute. In an embodiment, as may be seen in FIG. 5, the interval median calculation better compensates for erroneous values.

In a further example according to an embodiment of the present invention, the table of data below (Table 2) may be provided to illustrate the impact of using median interval values, in particular, using medians of the medians or medians of the means.

the median of the means is used (or mean of means—not shown), the effect of the original artifact may not be fully excluded. Using the data from Table 2, for example, if a calibration is performed at minute 11, 12 or 13, then the calibration value is accurate even if the median of means is used, but if a calibration is performed at minute 8, 9 or 10, then the calibration contains the original error. As shown in Table 2, when the median method (filter) is used, the method correctly classifies the data as hypoglycemic (less than 70 mg/dl) throughout the tracing, but when using the mean, for about 50% of the time, the system misclassifies the values as normoglycemic.

TABLE 2

Interval and Displayed Values

| | INTERVAL VALUES (assume sensitivity of 0.62 nA/(mg/dl)) | | | | DISPLAYED VALUES (assume sensitivity of 0.62 nA/(mg/dl)) | | | |
|---|---|---|---|---|---|---|---|---|
| | | | | | Median of Medians Over 5 Minutes | Median of Medians Over 5 Minutes | Median of Means Over 5 Minutes | Median of Means over 5 Minutes |
| Min | Median (nA) | Median (glucose) | Mean (nA) | Mean (glucose) | (nA) | (glucose mg/dl) | (nA) | (glucose mg/dl) |
| 1 | 44.0 | 71.0 | 51.0 | 82.3 | | | | |
| 2 | 44.5 | 71.8 | 45.2 | 72.8 | | | | |
| 3 | 41.0 | 66.1 | 32.0 | 51.6 | | | | |
| 4 | 41.5 | 66.9 | 41.8 | 67.5 | | | | |
| 5 | 40.5 | 65.3 | 41.2 | 66.4 | 41.5 | 66.9 | 41.8 | 67.5 |
| 6 | 42.0 | 67.7 | 55.7 | 89.8 | 41.5 | 66.9 | 41.8 | 67.5 |
| 7 | 44.0 | 71.0 | 51.0 | 82.3 | 41.5 | 66.9 | 41.8 | 67.5 |
| 8 | 44.5 | 71.8 | 45.2 | 72.8 | 42.0 | 67.7 | 45.2 | 72.8 |
| 9 | 41.0 | 66.1 | 32.0 | 51.6 | 42.0 | 67.7 | 45.2 | 72.8 |
| 10 | 41.5 | 66.9 | 41.8 | 67.5 | 42.0 | 67.7 | 45.2 | 72.8 |
| 11 | 40.5 | 65.3 | 41.2 | 66.4 | 41.5 | 66.9 | 41.8 | 67.5 |
| 12 | 42.0 | 67.7 | 55.7 | 89.8 | 41.5 | 66.9 | 41.8 | 67.5 |
| 13 | 44.0 | 71.0 | 51.0 | 82.3 | 41.5 | 66.9 | 41.8 | 67.5 |
| 14 | 44.5 | 71.8 | 45.2 | 72.8 | 42.0 | 67.7 | 45.2 | 72.8 |
| 15 | 41.0 | 66.1 | 32.0 | 51.6 | 42.0 | 67.7 | 45.2 | 72.8 |
| 16 | 41.5 | 66.9 | 41.8 | 67.5 | 42.0 | 67.7 | 45.2 | 72.8 |
| 17 | 40.5 | 65.3 | 41.2 | 66.4 | 41.5 | 66.9 | 41.8 | 67.5 |
| 18 | 42.0 | 67.7 | 55.7 | 89.8 | 41.5 | 66.9 | 41.8 | 67.5 |

Figure 6:
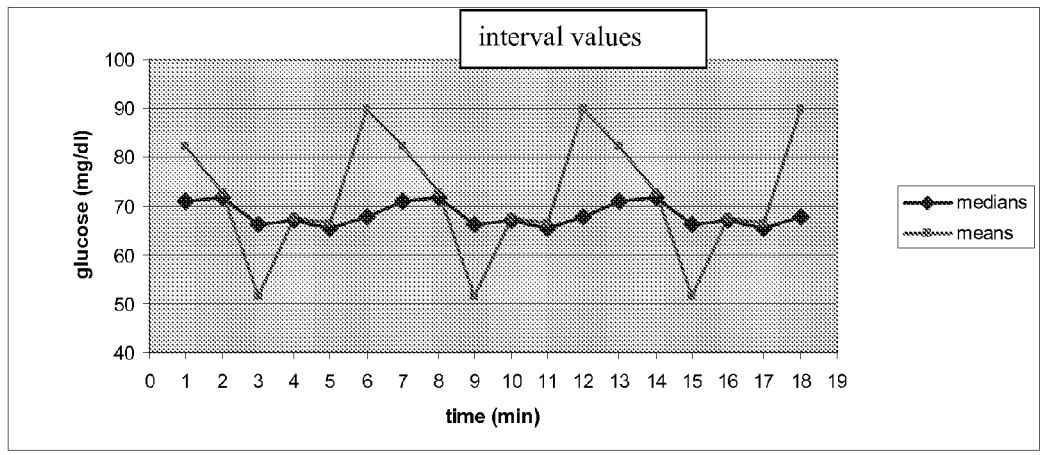
FIG. 6 illustrates a graph of interval medians and interval means in accordance with an embodiment of the present invention.

As shown in Table 2, the median values and mean values (interval values) shown are repeated every six minutes to provide a larger sample set for the example. FIG. 6 provides a plot of these data distinguishing the median and mean value calculation approaches. Although the term "displayed values" is used above in Table 2, in embodiments of the present invention, the raw data or the interval data may also be displayed with or without the displayed data. The term displayed data is utilized to identify the data which is most refined of the three choices (raw, interval, displayed) and thus, in embodiments, may be the preferred data for display.

In an embodiment of the present invention, before displaying values on an EMU, an additional computation may be run: a running median of the most recent 5 minute segment (a median of the medians). Such a calculation may be conducted for a variety of previous time periods other than 5 minutes, such as, for example, from 3 to 10 minutes.

In an alternative embodiment, a running median of the means may be calculated, which provides some correction of error found in the means themselves.

Figure 7:
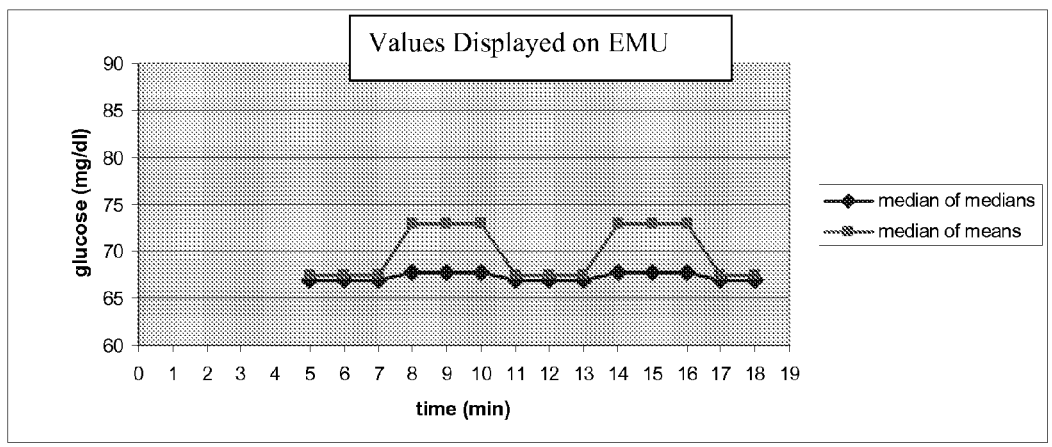
FIG. 7 illustrates a graph of medians of medians and medians of means in accordance with an embodiment of the present invention.

Note in Table 2 above, and FIG. 7, that the running median of the medians gives a relatively smooth data set but the running median of the means continues to show evidence of the original artifact.

In an embodiment, for a calibration, the median of medians may be used, which may better exclude the erroneous data. If Calibration errors are serious errors because they persist until the next calibration. Error in calibration may be minimized by using all or many of the previous calibrations, and/or by utilizing median values or medians of the medians. In an embodiment, using a moving median of the means may be better than using a moving mean of the means (moving average), but may not be as accurate as using a moving medians of the medians. In utilizing multiple data points, in an embodiment, the more remote calibrations may be underweighted to further improve accuracy.

In an embodiment, using all or most of the measured data points as described above may be better than eliminating one or more data points. For example, even if the highest and lowest of the raw data points are excluded over each minute, artifact may persist. When there is more than one erroneous low value in one minute or more than one erroneous high value in one minute, eliminating the high and/or the low data point will not completely exclude the erroneous values.

In an embodiment of the present invention, a physiological filter may also be applied to a stream of data. A physiological filter is programmed to recognize the acceptable ranges of analyte measurement and/or the acceptable rates of change of such an analyte. For example, it is known that glucose levels in a body do not increase by more than about 6-10 mg/dl per minute due to absorption of carbohydrate from the intenstine after feeding or from conversion of glycogen to glucose in the liver, and subsequent release from the liver into the bloodstream, during a fasting state. In addition, glucose levels in a body generally do not decrease any faster than about 6-10 mg/dl per minute because, to fall, glucose must generally be taken up by muscle cells, fat cells or brain cells and there is limit to the rate of the cellular uptake. Thus, when glucose levels appear to rise or fall faster than the physiological limit, a physiological filter may be used to exclude those values and instead use the limit value of the acceptable range.

In an embodiment of the present invention, a system or apparatus may be provided to implement the methods described herein. In an embodiment, an on-skin sensor control unit may be coupled to a biosensor. The on-skin sensor control unit may include a processor with programming instructions configured to implement the methods of embodiments of the present invention.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A method of calibrating a biosensor that measures an analyte, comprising:
    obtaining, by a computing device, a plurality of biosensor output signal values during a plurality of intervals;
    determining, by the computing device, a median interval sensor output value for each of the plurality of intervals;
    applying, by the computing device, a median filter to the median interval sensor output values to obtain a sensor output value representing a median value of the median interval sensor output values;
    comparing, by the computing device, a blood analyte concentration with the sensor output value to obtain a sensor sensitivity value; and
    utilizing, by the computing device, the sensor sensitivity value to calibrate signal output of the biosensor.

2. The method of claim 1, wherein at least one of the plurality of biosensor output signal values is obtained between 4 and 10 minutes after obtaining the blood analyte concentration.

3. The method of claim 1, wherein at least one of the plurality of biosensor output signal values is obtained about 5 minutes after obtaining the blood analyte concentration.

4. The method of claim 1, further comprising obtaining the blood analyte concentration by obtaining a blood sample via a fingerstick and using an external analyte meter to measure the blood analyte concentration of the blood sample.

5. The method of claim 4, wherein obtaining the blood analyte concentration comprises obtaining a plurality of blood analyte concentrations.

6. The method of claim 5, further comprising obtaining a sensor sensitivity value for each blood analyte concentration obtained, and wherein the sensor sensitivity values are temporally weighted.

7. The method of claim 1, wherein the signal output is displayed as a value on an electronic monitoring unit.

8. The method of claim 1, further comprising obtaining a value for a background current for the biosensor and subtracting, by the computing device, the background current value from the plurality of biosensor output signal values or from the median sensor output values prior to obtaining the sensor sensitivity value.

9. The method of claim 1, further comprising applying, by the computing device, a physiological filter to the plurality of biosensor output signal values.

10. The method of claim 1, wherein the biosensor comprises a glucose sensor.

11. The method of claim 1, wherein the analyte is glucose.

12. The method of claim 1, wherein the sensor sensitivity value is obtained by extrapolating, by the computing device, a line or curve to a fixed background current at zero glucose.

13. The method of claim 12, wherein the background current is calculated to be a fraction or multiple of the biosensor output signal values at zero glucose.

14. A method of sensing an analyte using a biosensor, comprising:
    obtaining, by a computing device, a plurality of biosensor output signal values during a plurality of intervals;
    determining, by the computing device, a median interval sensor output value for each of the plurality of intervals;
    applying, by the computing device, a median filter to the median interval sensor output values to obtain a sensor output value representing a median value of the median interval sensor output values; and
    displaying the sensor output value on an electronic monitoring unit coupled to the biosensor.

15. The method of claim 14, further comprising obtaining a value for a background current for the biosensor and subtracting, by the computing device, the background current value from the plurality of biosensor output signal values or from the sensor output value prior to displaying the sensor output value.

16. The method of claim 14, further comprising applying, by the computing device, a physiological filter to the plurality of biosensor output signal values.

17. The method of claim 14, wherein the biosensor comprises a glucose sensor.

18. The method of claim 14, wherein the analyte is glucose.

* * * * *